United States Patent

Hardy

[11] Patent Number: 6,145,507
[45] Date of Patent: Nov. 14, 2000

[54] ABBREVIATED CONDOM DEVICE

[76] Inventor: Timothy J. Hardy, 3720 Holland Rd., Suite 101, Virginia Beach, Va. 23452

[21] Appl. No.: 09/295,173

[22] Filed: Apr. 20, 1999

[51] Int. Cl.[7] .......................................................... A61F 6/04
[52] U.S. Cl. ............................................ 128/844; 128/918
[58] Field of Search .................... 128/842, 844, 128/918; 604/347–353

[56] References Cited

U.S. PATENT DOCUMENTS

| | | | |
|---|---|---|---|
| 4,332,243 | 6/1982 | Gutnick | 128/844 |
| 4,795,425 | 1/1989 | Pugh | 128/844 |
| 4,820,290 | 4/1989 | Yahr | 604/349 |
| 4,821,742 | 4/1989 | Phelps, III | 128/842 |
| 4,869,269 | 9/1989 | Sharken | 128/844 |
| 5,421,350 | 6/1995 | Friedman | 128/844 |
| 5,458,114 | 10/1995 | Herr | 128/844 |

*Primary Examiner*—Michael A. Brown
*Attorney, Agent, or Firm*—Webb Ziesenheim Logsdon Orkin & Hanson, P.C.

[57] ABSTRACT

A contraceptive device comprised of an abbreviated condom and an applicator therefor is disclosed. The abbreviated condom is adhesively applied to the glans penis of a male sex organ, leaving exposed the coronal sulcus for improved sensitivity. The adhesive coats only the peripheral area of the condom leaving a central area substantially adhesive-free, thereby forming a fluid receptacle in the area of the glans penis. A spermicide is contained within the fluid receptacle by a spermicide-releasing membrane for release after application.

7 Claims, 2 Drawing Sheets

ABBREVIATED CONDOM DEVICE

BACKGROUND OF THE INVENTION

1. Field of the Invention

This invention relates to an abbreviated condom device, more particularly, an abbreviated condom device for use as both a contraceptive device and a device for the prevention of the spread of sexually transmitted diseases.

2. Description of the Prior Art

The use of condoms as contraceptive devices and for preventing the spread of sexually transmitted diseases such as gonorrhea, chlamydia, auto-immune deficiency disease (AIDS) and the like, which are transmitted during sexual intercourse are well known. Although the use of condoms for these purposes has been well known for many years, the use of such devices has often been avoided due to the loss of sensitivity during sexual intercourse that can result.

The conventional condom typically consists of an elongated closed-end sheath, the sleeve of which is rolled down toward the closed end to form a disk configuration prior to application. Because conventional condoms sheath the coronal sulcus ("the corona"), the most sensitive area of the penis, the use of such devices results in a lack of sensitivity during sexual intercourse. The construction of the conventional condom requires that the device be applied to a tumescent penis to enable the sleeve to be unrolled downward over the penis to ensure a fit that will prevent the condom from being dislodged during intercourse. This is a particular disadvantage to older men as well as to those who have difficulty achieving or sustaining an erection.

Attempts have, heretofore, been made to overcome the problems associated with conventional condoms, that is, the lack of sensitivity during sexual intercourse and the necessity that the condom be applied to a tumescent penis by employing the use of abbreviated condoms. Such devices reduce the area of the penis covered by the condom.

U.S. Pat. No. 4,820,290 describes an abbreviated condom comprising a thin impervious hood which is sized to be applied over the glans penis, and a relatively thick peripheral band connected to the open perimeter of hood. The band is sufficiently elastic to fit snugly around the penis proximal to the corona to prevent dislodging of the condom during intercourse, but will allow expansion if applied to a pretumescent penis. However, because this device is configured to cover the corona, the problem of diminished sensitivity remains.

U.S. Pat. No. 4,821,742 discloses an abbreviated condom device which is adhesively applied to the glans penis, leaving the corona, the most sensitive area, exposed. The device of this reference employs pressure sensitive adhesive located around the inner periphery of the device to secure the condom to the glans penis. The center area of the inner surface which is to be applied over the external meatus, or glans penis opening is adhesive free, as are areas radiating outwardly from this area to provide a receptacle area. The device of this reference provides improved sensitivity during sexual intercourse and allows application to a pretumescent penis. However, the pressure sensitive adhesive employed to secure the device to the glans penis can result in problems with initial application and proper positioning. Moreover, because of excellent adherence to the skin, the condom can be difficult to remove. A need therefore remains for an abbreviated condom which does not sheath the corona area, and is both easy to apply and readily removable.

Additionally, the above-described prior art condoms are comprised of rubber and/or latex materials. Latex, however, is known to bring about an allergic reaction in increasing numbers of individuals every year. Also, since latex does not conduct heat as well as some other elastic materials, a portion of the loss of sensitivity with the use of latex condoms can be attributed to the latex material itself. A need therefore remains for a non-latex condom which additionally satisfies the above-described objectives.

SUMMARY OF THE INVENTION

In order to meet this need, a contraceptive device is provided which is comprised of an abbreviated condom for adhesive application to the glans penis of a male sex organ and an applicator therefor. The condom is comprised of a body which is shaped, sized and adapted for substantially covering the glans penis while allowing the corona surrounding the glans penis to be exposed. When applied, the condom forms a fluid enclosure over the opening of the glans penis and the surrounding area. The peripheral area of the inner surface of the condom is continuously coated with a pressure sensitive adhesive for forming a fluid tight seal with the glans penis. Surrounded by the adhesive coating, the central area of the condom inner surface is adhesive-free for positioning over the glans penis opening wherein a portion of the central area extends outwardly from the glans penis opening to form a fluid reservoir therebetween. The fluid reservoir contains therein a spermicide, which is held within the fluid reservoir and separated from the glans penis by a spermicide-releasing membrane for release subsequent to application.

The plastic applicator is comprised of an applicator head which has a concave inner surface and is sized and adapted for receiving and securing therein the convex outer surface of the condom body, thereby substantially maintaining the semi-spherical shape thereof prior to application to the glans penis.

A complete understanding of the invention will be obtained from the following description when taken in connection with the accompanying drawing figures wherein like reference characters identify like parts throughout.

Other objects and features of the invention will appear in the course of the description thereof, which follows.

DETAILED DESCRIPTION OF THE INVENTION

Figure 1:
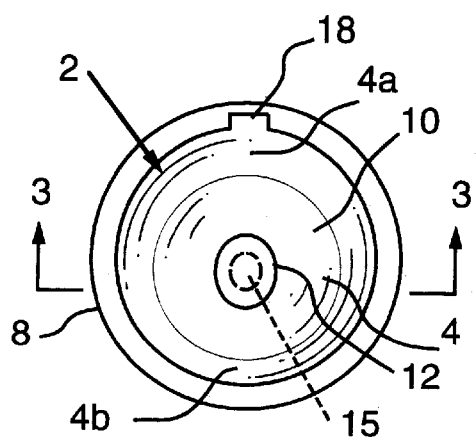
FIG. 1 is a top view of the condom device of the invention as applied to the glans penis.

With reference to FIGS. 1–4, the condom of the present invention, generally designated as 2, includes a base 4 of flexible, elastic material selected from the group consisting of latex and vinyl, preferably vinyl, for adhesive application to a glans penis 6, having a corona 8, a shaft 9 and a glans penis opening 11; and a plastic applicator 19. A vinyl material is preferred for the condom of the present invention because this material can avoid the allergic reactions often associated with latex materials. Also, since vinyl is a better heat conductor, some of the loss of sensitivity associated with the use of latex condoms can be avoided.

For purposes which will later be described, condom 2 has a central area 13 for positioning over and around the glans penis opening 11 and a fluid reservoir 12 extending outwardly from central area 13, both integral with base 4. The fluid reservoir 12 preferably defines a volume of about 8 cubic centimeters (c.c.).

Except for the outwardly extending fluid reservoir 12, formed integrally with base 4, base 4 is of substantially semi-spherical shape and is coated on its inner surface with a pressure sensitive adhesive 14, leaving the central area 13 and fluid reservoir 12 free of adhesive.

The pressure sensitive adhesive coating 14 can be any of the variety of the pressure sensitive adhesives as are well known in the art. Preferably, however, the pressure sensitive adhesive coating is a low mass transfer material with a substantial resistance to lifting or pulling. The preferred pressure sensitive adhesives have a peel force (i.e., the force required to remove an adhesive-coated tape (2.5 cm×7.5 cm) which has been applied to human skin) of less than 12 N/dm, more preferably from about 2.0 N/dm to about 8.0 N/dm, and most preferably from about 3.5 N/dm to about 6.0 N/dm when adhered to skin. Suitable examples include the acrylic-based adhesives which contain an unreacted polyol plasticizer as described in U.S. Pat. No. 4,140,115 and the hydrophobic polyoxyalkylene-based adhesives derived from poly(ethylene glycol) prepared in the presence of a plasticizer as described in U.S. Pat. No. 5,536,768. Also suitable for use in the invention are the silicone-based pressure sensitive adhesives described in U.S. Pat. No. 4,460,371 and the medical adhesives comprised of an acrylic pressure sensitive adhesive and one of an elastomer with a tackifying resin or a thermoplastic elastomer as described in U.S. Pat. No. 5,876,855.

Figure 2:
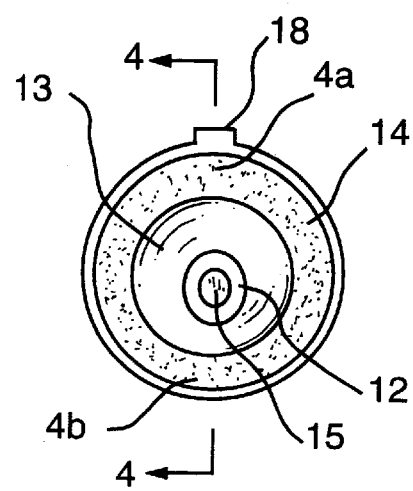
FIG. 2 is a bottom view of the device of FIG. 1 prior to application to the glans penis.
Figure 3:
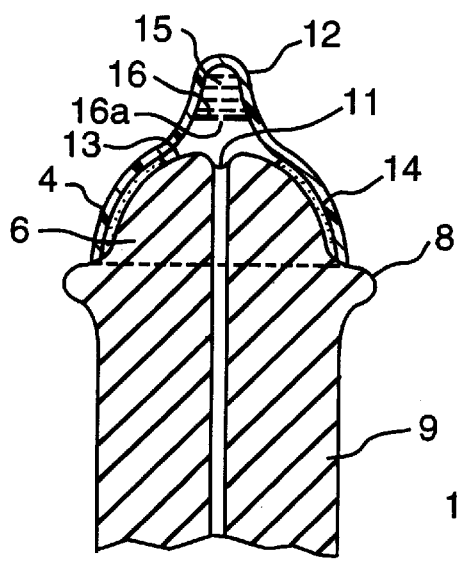
FIG. 3 is a section view taken at 3—3, FIG. 1.
Figure 4:
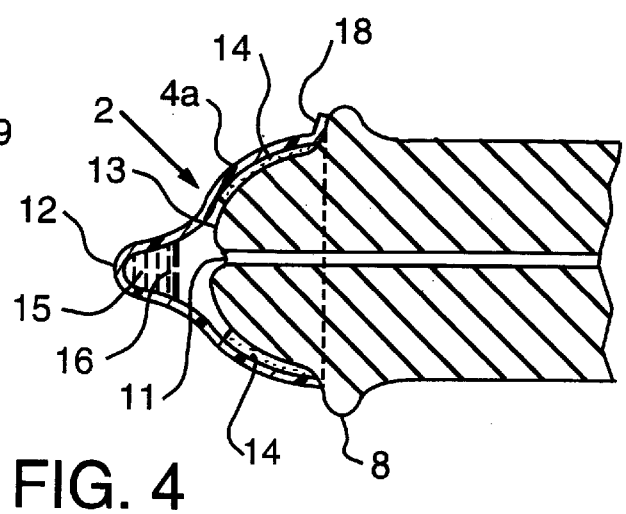
FIG. 4 is a section view taken at 7—7, FIG. 2.

As best shown in FIGS. 1, 2 and 4, the top or dorsal side 4a of condom 2 is longer than the bottom or ventral side 4b, to better conform with the glans penis 6. In a preferred embodiment of the present invention, at the top or dorsal side 4a, base 4 is provided with a tab 18 formed integrally with base 4 and extending outwardly therefrom. Preferably, tab 18 is not coated with adhesive, and provides a means for removing the condom 2 from the glans penis 6 after use. Tab 18 also provides a point of reference for locating the longer dorsal or top side 4a of base 4 for application of condom 2 to the glans penis 6.

Figure 5:
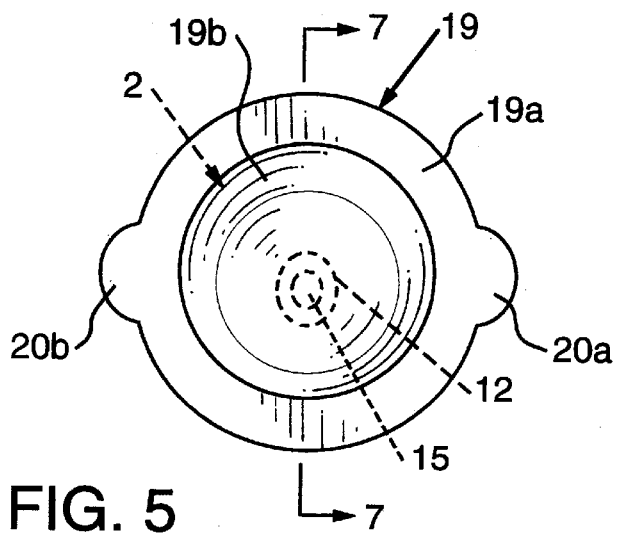
FIG. 5 is a top view of the device of FIG. 1 as secured within the applicator 19.
Figure 6:
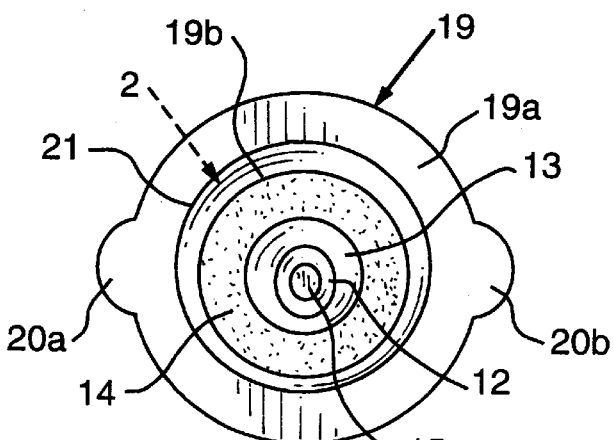
FIG. 6 is a bottom view of the device of FIG. 5.
Figure 7:
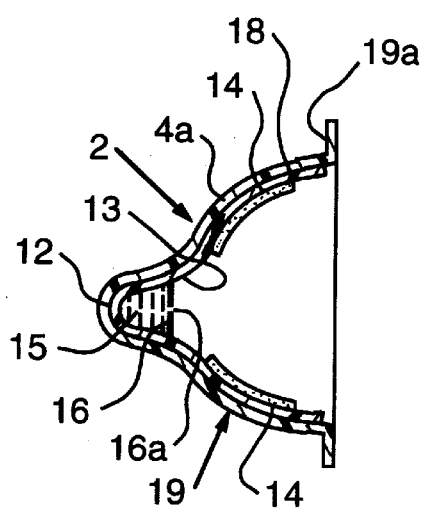
FIG. 7 is a section view of the device of FIG. 5, taken at 7—7, FIG. 1.

Within the fluid reservoir 12 is contained a spermicide 15, preferably Nonoxynol-9. Spermicide 15 is present in the fluid reservoir 12 in an amount from about 1.5 c.c. to about 2.5 c.c. The spermicide 15 is held within fluid reservoir 12 and separated from the glans penis 6 opening by a thin plastic spermicide-releasing membrane 16. The spermicide-releasing membrane 16 is attached about its circumference to the inner surface of fluid reservoir 12 and has at its center point a single perforation 16a. The spermicide-releasing membrane 16 is typically a very thin plasticized film, for example, a polyvinyl chloride film, typically from about 5 to about 100 microns, preferably about 25 to 75 microns, and more preferably about 30 to 50 microns, in thickness. Subsequent to application of condom 2 to the glans penis 6, but prior to removal of the applicator 19, the fluid reservoir 12 is gently compressed. This pressure coupled with perforation 16a causes the thin plastic spermicide-releasing membrane 16 to lose integrity, thereby releasing the spermicide 15 into the fluid reservoir 12 and the adhesive-free center area 13 of the inner surface of condom 2. Thus the spermicide 15 comes in contact only with the glans penis 6. As best depicted in FIGS. 5–7, the applicator 19, open at end 21, is comprised of a rim 19a and an applicator head 19b. Applicator 19 is a flexible, deformable plastic, for example low density polyethylene or polypropylene, sized and adapted to receive and secure therein the convex outer surface of condom 2. Rim 19a is integral with and extends radially outward from and normal to the open end 21 of applicator 19. Grips 20a and 20b, disposed opposite one another at position 3—3, are each integral with and extend outwardly from the peripheral edge of rim 19a for use in application of condom 2 to the glans penis 6.

Generally, while holding grips 20a and 20b, condom 2 is positioned such that the adhesive-free center area 13 of the inner surface of condom 2 is positioned directly over and around the glans penis opening 11 such that fluid reservoir 12 extends outwardly from the glans penis opening 11. Tab 18 provides a reference point for locating the longer dorsal on the top side 4a of base 4 of condom 2. Once positioned, the adhesive 14 is made to contact the glans penis 6 by manual application of pressure to the outside surface of applicator 19. Applicator 19 is then removed and discarded. Subsequent to application, the fluid reservoir 12 is compressed by applying pressure to the outside surface of the applicator 19 in the area surrounding the fluid reservoir 12, to release the spermicide 15 by disrupting the integrity of the spermicide-releasing membrane 16 via perforation 16a.

Figure 8:
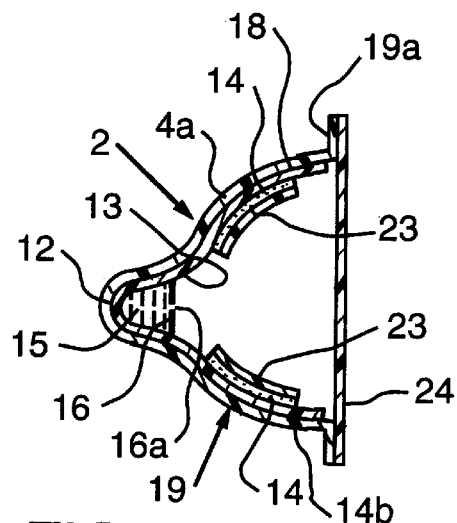
FIG. 8 is a section view of the device of FIG. 5, wherein the applicator 19 serves as a package for the condom device of the invention.

As depicted in FIG. 8, applicator 19 may optionally serve as a portion of the packaging for the abbreviated condom of the invention. For purposes of storage and handling, the pressure sensitive adhesive coating can be covered with a protective strip 23, for example, a coated paper or thin plastic protective strip, that can easily be peeled off prior to application without damaging the adhesive or the inner surface of the condom body. Once the condom 2 is placed and secured within the applicator 19 package, the open end 21 of the applicator 19 package can be removably sealed with a plastic film 24.

While the foregoing embodiments of the present invention have been set forth in considerable detail for the purpose of making a complete disclosure of the invention, it may be apparent to those of skill in the art that numerous changes may be made in such detail without departing from the spirit and principles of the invention.

What is claimed is:

1. A contraceptive device comprising:
    (a) an abbreviated condom for adhesive application to the glans penis of a male sex organ, said condom comprising:
        a condom body shaped, sized and adapted for substantially covering the glans penis while allowing the corona surrounding the glans penis exposed, said body having a concave inner surface, a convex outer surface, and a peripheral edge, said inner surface having a central area and a peripheral area;
        said condom forming a fluid enclosure over the opening of the glans penis and the area therearound;
        said condom on the inner surface thereof to be applied to the glans penis and having a pressure sensitive adhesive coating thereon;
        said adhesive coating being continuous around the peripheral area of the inner surface for forming a fluid tight seal with the glans penis;

said central area of the inner surface being adhesive free and surrounded by the adhesive coating for positioning over the glans penis opening wherein a portion of the central area extends outwardly from the glans penis opening to form a fluid reservoir therebetween;

said fluid reservoir containing therein a spermicide, said spermicide being held within the fluid reservoir and separated from the glans penis by a spermicide-releasing membrane;

wherein said condom is comprised of a material selected from the group consisting of vinyl materials and latex materials; and (b) a plastic applicator comprising an applicator head having a concave inner surface, shaped, sized and adapted for receiving and securing therein the convex outer surface of said condom body, thereby substantially maintaining the shape thereof prior to application to the glans penis.

2. The contraceptive device of claim 1 wherein the pressure sensitive adhesive is selected from the group consisting of polyoxyalkylene-based adhesives, acrylic-based adhesives, and silicone-based adhesives.

3. The contraceptive device of claim 1 wherein the condom is comprised of a vinyl material.

4. The contraceptive device of claim 1 wherein the spermicide is Nonoxynol-9.

5. The contraceptive device of claim 1 wherein the condom further comprises at least one tab integral with and extending outwardly from the peripheral edge of the condom body.

6. The contraceptive device of claim 1 wherein the fluid reservoir defines a volume of about 8 cubic centimeters.

7. The contraceptive device of claim 6 wherein the spermicide is present in the fluid reservoir in an amount of from about 1.5 to about 2.5 cubic centimeters.

* * * * *